US010058312B2

(12) United States Patent
Lalonde

(10) Patent No.: US 10,058,312 B2
(45) Date of Patent: Aug. 28, 2018

(54) SYSTEMS AND METHODS FOR CRYOADHESIVE TRANSSEPTAL PUNCTURES

(75) Inventor: Jean-Pierre Lalonde, Candiac (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1367 days.

(21) Appl. No.: 13/281,927

(22) Filed: Oct. 26, 2011

(65) Prior Publication Data

US 2013/0110148 A1 May 2, 2013

(51) Int. Cl.
| A61B 18/02 | (2006.01) |
| A61B 17/00 | (2006.01) |
| A61B 18/00 | (2006.01) |
| A61B 90/00 | (2016.01) |

(52) U.S. Cl.
CPC ........ *A61B 17/00234* (2013.01); *A61B 18/02* (2013.01); *A61B 2017/00084* (2013.01); *A61B 2017/00247* (2013.01); *A61B 2018/0066* (2013.01); *A61B 2018/00357* (2013.01); *A61B 2018/00601* (2013.01); *A61B 2018/00714* (2013.01); *A61B 2018/00744* (2013.01); *A61B 2018/00791* (2013.01); *A61B 2018/00863* (2013.01); *A61B 2018/00875* (2013.01); *A61B 2090/065* (2016.02)

(58) Field of Classification Search
USPC ............ 606/2–21, 28, 37, 39, 167, 170, 185
See application file for complete search history.

(56) References Cited

U.S. PATENT DOCUMENTS

| 3,289,749 A | 12/1966 | Crump |
| 3,512,531 A | 5/1970 | Crump et al. |
| 3,951,152 A | 4/1976 | Crandell et al. |
| 5,281,213 A | 1/1994 | Milder et al. |
| 5,727,569 A | 3/1998 | Benetti et al. |

(Continued)

FOREIGN PATENT DOCUMENTS

| WO | 0054684 A1 | 9/2000 |
| WO | 2008000065 A1 | 1/2008 |

OTHER PUBLICATIONS

Knecht, S, et al, Radiofrequency Puncture of the Fossa Ovalis for Resistant Transseptal Access, Circ Arrhythm Electrophysiol 2008:,1:169-174; Dallas, TX—web page: http://circep.ahajournals.org/content/1/3/169.full.pdf.

(Continued)

*Primary Examiner* — Paula J Stice
(74) *Attorney, Agent, or Firm* — Christopher & Weisberg, P.A

(57) ABSTRACT

A cryogenic medical system and method of use thereof for transseptal puncturing is disclosed, including a medical device having an elongate body with a fluid flow path therein, a thermally-transmissive region coupled to the elongate body in thermal communication with the fluid flow path, and a puncturing element movably coupled to the elongate body; and a cryogenic coolant source in fluid communication with the fluid flow path. The medical device may alternatively include an elongate body, a thermally-transmissive region coupled to the elongate body, a thermoelectric cooler in thermal communication with the thermally-transmissive region, and a puncturing element movably coupled to the elongate body.

15 Claims, 4 Drawing Sheets

(56) References Cited

U.S. PATENT DOCUMENTS

| | | | |
|---|---|---|---|
| 5,836,311 | A | 11/1998 | Borst et al. |
| 5,894,843 | A | 4/1999 | Benetti et al. |
| 7,625,369 | B2* | 12/2009 | Abboud et al. ............. 606/21 |
| 7,794,454 | B2 | 9/2010 | Abboud et al. |
| 7,931,590 | B2 | 4/2011 | Willis |
| 8,346,373 | B2* | 1/2013 | Thompson-Nauman et al. ............ 607/122 |
| 2004/0002749 | A1 | 1/2004 | Joye et al. |
| 2006/0224153 | A1 | 10/2006 | Fischell et al. |
| 2007/0293724 | A1 | 12/2007 | Saadat et al. |
| 2008/0215008 | A1 | 9/2008 | Nance et al. |
| 2008/0243081 | A1 | 10/2008 | Nance et al. |
| 2009/0005769 | A1 | 1/2009 | Haywood |
| 2009/0118723 | A1 | 5/2009 | Lalonde et al. |
| 2009/0287201 | A1 | 11/2009 | Lalonde et al. |
| 2010/0191231 | A1 | 7/2010 | Heberer |
| 2010/0241113 | A1 | 9/2010 | Ingle |
| 2012/0029494 | A1 | 2/2012 | Wittenberger et al. |
| 2012/0259324 | A1* | 10/2012 | Brannan ................. 606/33 |

OTHER PUBLICATIONS

Google books, Small Animal Ophthalmic Surgery: Practical Techniques for the Veterinarian—web page: http://books.google.com/books?id=Uh1aDxe9XycC&pg=PA28&lpg=PA28&dq=ryoadhesion+temperature&source=bl&ots=a0FU_ZLJ&sig=eM6AmGDWTBmy-4iZGO89M1GzTgk&hl=en&ei=ujIVTvuYJMPPgAe8_6w2&sa=X&oi=book_result&ct=result&resnum=ved=0CDkQ6AEwBQ#v=onepage&q=cryoadhesion%20temperature&f=false.

The Study of Cryoadhesion in Cryoablation for Atrioventricular Nodal Reentrant Tachycardia, China Papers; web page: http://mt.china-papers.com/2/?p=76865.

Harurta, S., et al., The Guidewire Technique for Transseptal Punture, Journal of Invasive Cardiology; web page: http://www.invasivecardiology.com/article/3696.

Bhindi, R., et al., Mammoth interatrial septal aneurysm in the ICE age, Cardiovascular Ultrasound, 2007; web page: http://www.cardiovascularultrasound.com/content/5/1/30.

Earley, M., How to perform a transseptal puncture, Heart 2009;95:85-92.; web page: http://www.hruk.org.uk/Docs/Guidelines/How%20to%20perform%20a%20transeptal%20puncture%20EiH.pdf.

SafeSept™ Transseptal Guidewire; web page: http://www.pressure-products.com/pages/SafeSept_Page.html.

Finger, Paul T., "Fingertip" Cryoprobe Assisted Orbital Tumour Extraction, Br. J. Ophthalmol. 2005;80: pp. 777-778.

Finger, Paul T., "Finger-Tip" Cryoprobe Assisted Enucleation, American Journal of Ophtalmology, vol. 139, Issue 3, pp. 559-561.

CIPO, Jan. 23, 2013 International Search Report, pp. 1-4.

CIPO, Jan. 23, 2013 Written Opinion, pp. 1-5.

Canadian Intellectual Property Office First Official Action for Application No. 2,852,643, dated Sep. 8, 2015, 3-pages.

* cited by examiner

SYSTEMS AND METHODS FOR CRYOADHESIVE TRANSSEPTAL PUNCTURES

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to systems, devices, and methods for engaging and puncturing tissue.

BACKGROUND OF THE INVENTION

Many cardiac procedures are commonly performed in the left atrium of the heart, which is not easily accessible. In order to treat the left atrium, a device may enter the patient's circulatory system via the patient's femoral vein. The device may then be advanced through the femoral vein to the right atrium of the heart. Once in the right atrium, a transseptal puncture is typically created in the transseptal wall to gain access to the left side of the heart and associated vasculature.

Although transseptal puncture is commonly performed, life-threatening complications such as pericardial tamponade, aortic perforation, and systemic embolization may occur. Many of these occurrences are the result of unintentional puncturing of the atrial walls. For example, the beating of the heart, slipperiness of the myocardium, and irregularities in the thickness of the septum can contribute to the difficulty in steering a catheter or other device and accurately puncturing the septum without causing injury. Therefore, anchoring of the puncturing device against the tissue may be critical to the successful treatment of atrial fibrillation and other cardiac conditions that involve transseptal puncture.

Stabilization and/or anchoring of the cardiac tissue has been performed using devices that apply mechanical or compression force, such as clamps, or devices that apply negative pressure (i.e. suction) to the tissue. However, these devices are sometimes significantly invasive, requiring insertion through the rib cage. Furthermore, such devices may present excess force or trauma to the engaged tissue, causing unwanted injury to the patient.

Accordingly, in light of the above limitations, it would be desirable to provide systems, devices, and methods by which tissue could be effectively and safely engaged and punctured in a minimally invasive fashion, thereby reducing the risk of life-threatening complications.

SUMMARY OF THE INVENTION

The present invention advantageously provides systems, devices, and methods of use thereof by which tissue can be effectively and safely engaged and punctured in a minimally invasive fashion. In a particular embodiment, a tissue puncturing device is disclosed, including an elongate body defining a proximal portion, a distal portion, a fluid flow path, and a lumen; a cryoadhesive segment coupled to the distal portion of the elongate body and in thermal communication with the fluid flow path; and a puncturing element movably disposed within the lumen. The lumen may be thermally insulated. The device may include a cryogenic coolant source in fluid communication with the fluid flow path; a sensor coupled to the distal portion of the elongate body; and/or a control unit in communication with the sensor, where the control unit is programmed to regulate fluid flow to the fluid flow path based at least in part on a signal from the sensor. The sensor may include a temperature sensor; a pressure sensor; and/or a flow rate sensor. The device may further include a Peltier device. The control unit may be programmed to maintain a temperature of the cryoadhesive segment within a predefined temperature range, such as between approximately 0° C. and approximately −30° C. The cryoadhesive segment may circumscribe the lumen, and the puncturing element may include a needle and/or a guide wire.

In another particular embodiment, a tissue puncturing device is disclosed, including an elongate body defining a proximal portion, a distal portion, and a lumen; a thermally-transmissive region coupled to the distal portion of the elongate body; a thermo-electric cooler in thermal communication with the thermally-transmissive region; and a puncturing element movably disposed within the lumen. The thermo-electric device may be a Peltier cooler.

A cryogenic medical system is disclosed, including a medical device including an elongate body having a fluid flow path therein, a thermally-transmissive region coupled to the elongate body in thermal communication with the fluid flow path, and a puncturing element movably coupled to the elongate body; and a cryogenic coolant source in fluid communication with the fluid flow path. The system may include a control unit coupled to the cryogenic coolant source, the control unit programmed to regulate fluid delivery from the cryogenic coolant to the medical device. The control unit may be programmed to regulate fluid delivery to substantially maintain a temperature of the thermally-transmissive region between approximately 0° C. and approximately −30° C.

A method of transseptal puncture is disclosed, including positioning a thermally-transmissive region of a medical device in contact with a septum; delivering a coolant to the medical device to cool the thermally-transmissive region; cryoadhering the thermally-transmissive region to the septum; and puncturing the septum with a puncturing element. The thermally-transmissive region may be cooled to a temperature between approximately 0° C. and approximately −30° C. The method may include monitoring the temperature of the thermally-transmissive region; adjusting the delivery of coolant in response to the monitored temperature; and/or passing a secondary device through the medical device and through the punctured septum

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1A:
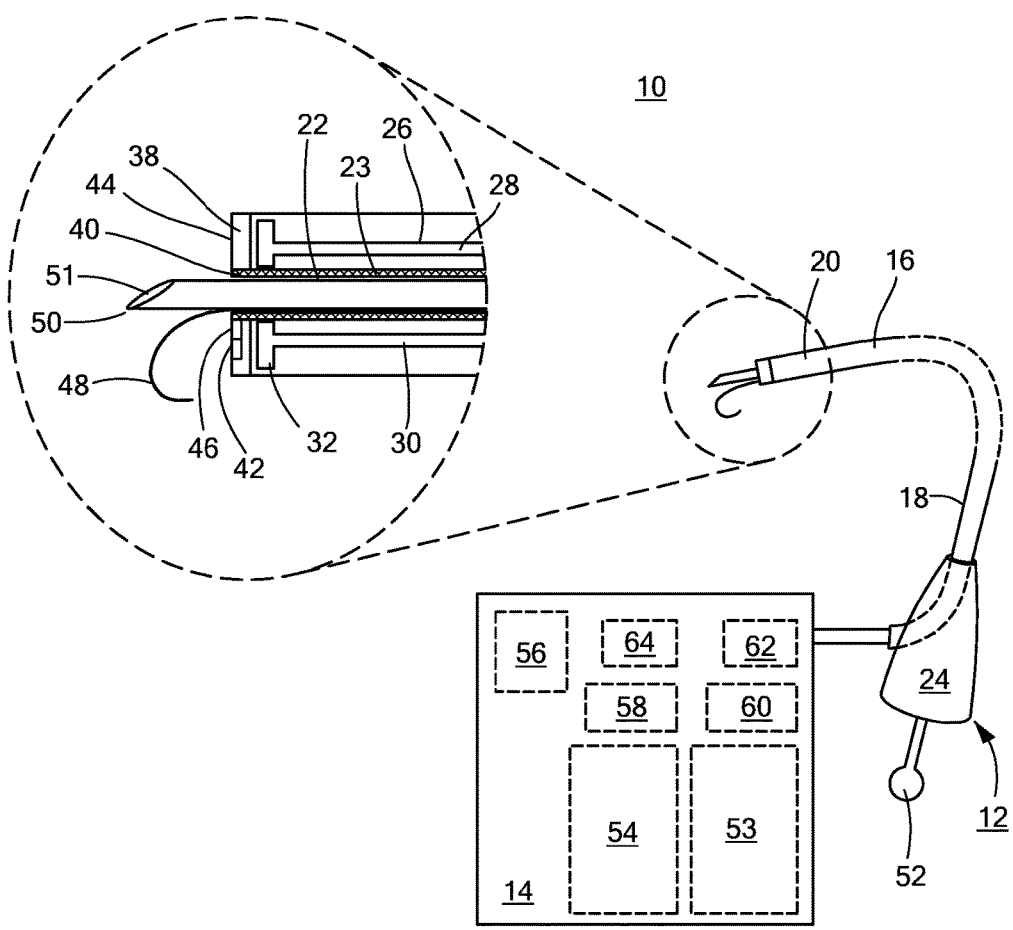
FIG. 1A illustrates an example of a system for tissue anchoring and puncturing in accordance with the present disclosure.

The present invention provides systems and methods of use thereof for anchoring tissue using cryoadhesion while puncturing the tissue during various medical procedures. For example, the systems and methods of use thereof could be used for performing transseptal punctures to gain access to otherwise inaccessible or difficult-to-reach tissue regions, such as the left atrium. Referring now to the drawing figures in which like reference designations refer to like elements, FIG. 1 shows a system 10 for engaging and puncturing tissue, such as a septum. The system 10 may generally include a device 12 for anchoring tissue and performing transseptal punctures and a control unit 14 for operating, monitoring, and regulating the operation of the device 12.

Figure 1B:
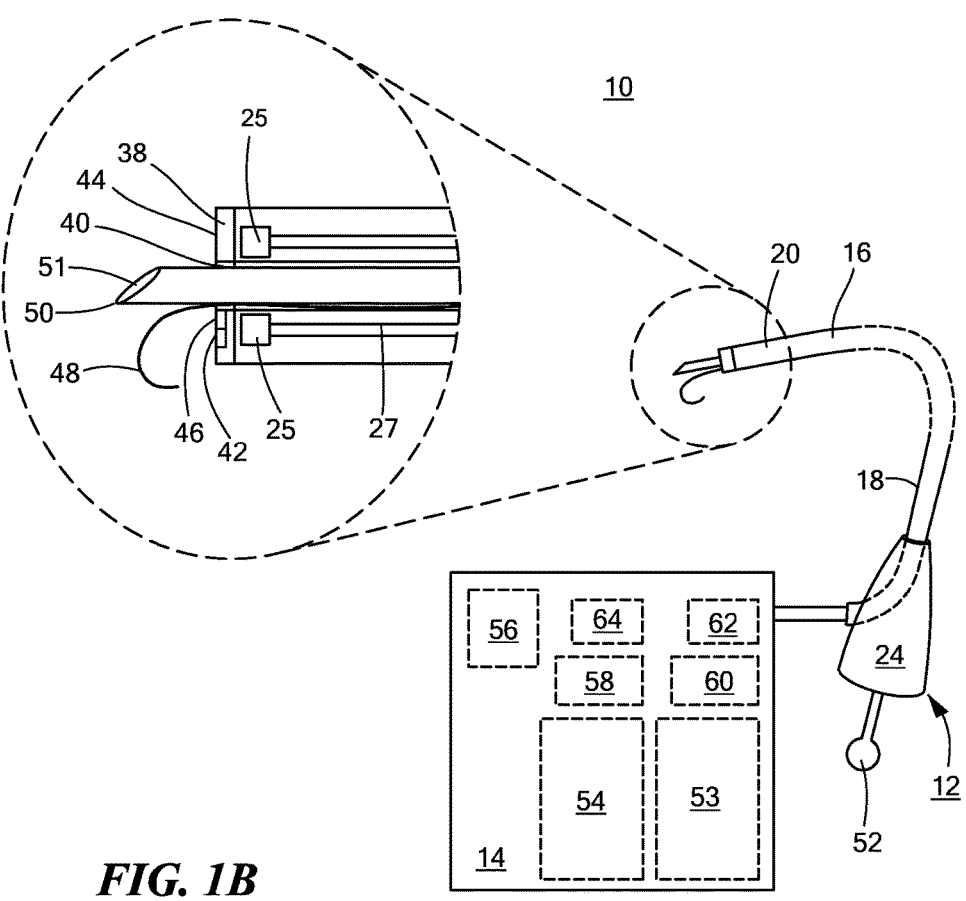
FIG. 1B illustrates an alternative embodiment of the system for tissue anchoring and puncturing in accordance with the present disclosure.
Figure 2:
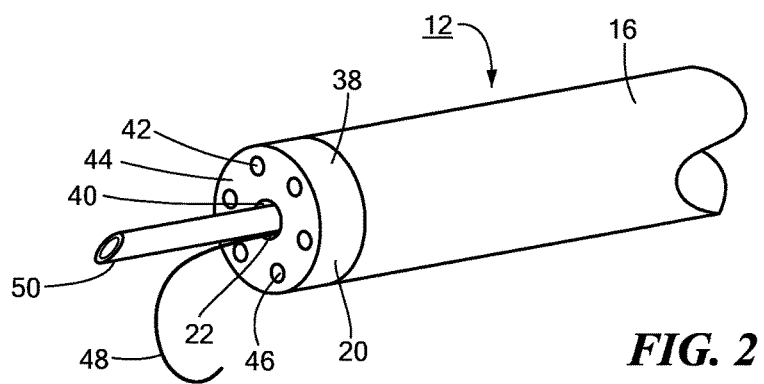
FIG. 2 illustrates a perspective view of the device of the system in FIG. 1.

Referring now to FIGS. 1 and 2, the device 12 may include a flexible elongate body 16 having a proximal portion 18, a distal portion 20, and a lumen 22. The elongate body 16 may include a flexible catheter body suitable for intravascular procedures. The elongate body 16 may define one or more secondary lumens disposed within providing mechanical, electrical, and/or fluid communication between the proximal portion 18 of the elongate body 16 and the distal portion 20 of the elongate body 16. The lumen 22 may be thermally insulated 23 to substantially prevent heat exchange between, for example, the lumen 22 (and any devices or components therein) and the coolant.

The proximal end 18 of the elongate body 16 may be coupled to a handle 24, which may include various ports for electrical and fluid connectors, leads, junctions, or tubes, and may also include various control assemblies, such as switches or valves, as well as safety detection or shutdown components. For example, the handle 24 may include connectors that are matable directly or indirectly by way of one or more umbilicals to the control unit 14. Further, the handle 24 may also include an element such as a lever or knob for manipulating or deflecting at least a portion of the elongate body 16.

The device 12 may further include a fluid flow path 26 disposed within, as shown in FIG. 1A. The fluid flow path 26 may include one or more lumens defined by the elongate body 16. For example, the fluid flow path 26 may include a coolant injection line 28, a coolant return line 30, and may include an expansion chamber 32 to facilitate a phase change in a pressurized coolant, resulting in a temperature reduction within a distal portion of the device 12, as discussed below. The coolant injection line 28 and/or the coolant return line 30 may be in communication with one or more ports in communication with the fluid flow path 26 and located on or proximal to the handle 24. The one or more ports may facilitate ease of connection to a fluid source and/or the control unit 14.

The device 12 may further include a thermally-transmissive region 38 in thermal communication with the fluid flow path 26. The thermally-transmissive region 38 may be disposed on a distal portion of the elongate body 16 to facilitate engagement or anchoring of the device 12 against tissue to be punctured. As used herein, a "thermally transmissive region" is intended to broadly encompass any structure or region of the device 12 that readily conducts thermal energy. For example, the thermally-transmissive region 38 may include a metal structure exposed (directly or indirectly) to the fluid flow path 26. Thermally-conductive polymers or composites may also be implemented to achieve the desired thermal transfer as described herein. The thermally-transmissive region 38 may include a single, continuous, and uninterrupted surface or structure, or it may include multiple discrete thermally transmissive structures that collectively define a thermally-transmissive region. Further, the thermally transmissive region 38 may be coaxial to the lumen 22 of the elongate body 16 such that it substantially circumscribes an opening 40. Alternatively, the thermally transmissive region 38 may asymmetrically disposed about the distal region 20 of the device or traverse only a portion of the circumference of the elongate body 16 (either at or near the distal region 20). The thermally-transmissive region 38 may be selectively deformable or malleable to take on multiple desired shapes or configurations. Such configurations or shapes may be achieved through the implementation of shape memory materials, steering mechanisms, or other deformational mechanisms.

The device 12 may further include a puncturing element 50 movably disposed within the lumen 22 to create an opening in tissue engaged with the medical device. The puncturing element 50 may be any sufficiently pointed component capable of puncturing tissue, such as a needle. In another example, the puncturing element 50 may be a guide wire 48. The guide wire 48 may be insertable into the lumen 22 of the elongate body 16. Alternatively, the elongate body 16 may include a separate guide wire lumen (not shown) extending along at least a portion of the length of the elongate body 16 for over-the-wire applications. The puncturing element 50 may be removably or permanently coupled to the device 12 at either the handle 24 or at any point along the elongate body 16. Further, the puncturing element 50 may be disposed within the device 12 in an off-axis manner so as to allow the concurrent passage of a secondary device (or a guide wire) through the lumen 22. The puncturing element 50 may have a distal end 51 movable about the elongate body 16, and may include a number of different geometries or bevels (such as a point, conical reverse bevel or tangential back bevel) suitable to perform tissue puncture.

The device may further include a proximal puncture control element 52 coupled to the puncturing element 50 for the selective and controlled deployment of the puncturing element through the tissue. The puncture control element 52 may include a handle, hub, or other selectively controllable feature. In order to prevent or minimize inadvertent laceration of tissue 39 while the device 12 is being advanced through the patient's vasculature or being positioned within the heart, the puncturing element 50 may have a neutral position in which the tip of the puncturing element 50 is located within the device 12, away from the lumen opening 40 (as a non-limiting example, approximately 0.5 to approximately 3 inches from the lumen opening 40, toward the proximal end 18 of the device 12). The elongate body 16 may serve as an introducer for the puncturing element 50 during the tissue puncture. In addition, the medical device may further include a removable sheath and/or dilator (not shown) to facilitate entry of a post-puncture or secondary device through a transeptal puncture and into the left atrium.

The system 10 may further include one or more sensors to monitor the operating parameters throughout the system, including for example, pressure, temperature, flow rates, volume, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or coolant delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

In a particular example, the device 12 may further include one or more temperature sensors 42 coupled to the distal portion of the medical device. For example, the one or more sensors 42 may be located either on the external surface or within the lumen 22 of the elongate body 16, including a distal face 44 of the distal region 20. Further, the one or more temperature sensors 42 may be located adjacent to each other to form a single temperature-sensing region or they may be located at discrete locations along the elongate body 16. The one or more temperature sensors 42 may be in communication with the control unit 14 to provide for automated feedback control of one or more operating parameters of the system. For example, the measured temperature(s) may be communicated by the one or more temperature sensors 42 to the control unit 14, which may modify fluid delivery to the device 12 to maintain the thermally transmissive region 38 and/or tissue interfacing with the device within a designated temperature range.

The device 12 may further include one or more pressure sensors 46 coupled to the distal portion 20. The sensors 46 may be used to facilitate positioning of the device 12 within the patient's body, and may further provide monitoring of the engagement between the device 12 and a designated tissue region during a procedure. The one or more pressure sensors 46 may be in communication with the control unit 14. The one or more pressure sensors 46 may be located on the external surface of the elongate body 16, including the distal face 44. The sensors 46 may be adjacent to each other to form a single pressure-sensing region or they may be located at discrete locations along the elongate body 16.

In an exemplary system, a coolant source 53 including a coolant, cryogenic refrigerant, a coolant collection reservoir 54 and/or an exhaust or scavenging system (not shown) for recovering or venting expended fluid for re-use or disposal, as well as various control mechanisms for the medical system 10 may be housed in the control unit 14 and in communication with the medical device 16. The coolant source 53 and the coolant collection reservoir 54 each may include a discrete container removably housed within the control unit 14, or a discrete container connected to the control unit 14 and/or the medical device via one or more umbilicals, cables, tubes, and the like. A vacuum pump 58 in the control unit 14 may create a low-pressure environment in one or more conduits within the medical device 12 so that fluid is drawn into the conduit(s)/lumen(s) of the elongate body 16, away from the distal portion and towards the proximal portion of the elongate body 16. The control unit 14 may also include additional pumps, valves, controllers or the like (collectively "60") to regulate delivery, recovery and/or re-circulation of fluid delivered to the handle, the elongate body, and/or the fluid pathways of the medical device 12.

The control unit 14 may further include a user interface 56, which may include an LCD touch screen or other display device that displays status and data of the system 10, as well as accepting user data and control inputs. Various discrete indicators, controls, and displays may also be included which indicate the status of one or more control unit 14 parameters and allow inputs for manual operation of the system 10. The user interface 56 may include one or more visual displays and/or one or more electrical or mechanical input components. The control unit 14 may also include one or more controllers, processors, and/or software modules containing instructions or algorithms to provide for the automated operation and performance of the features, sequences, or procedures described herein.

The control unit 14 may be used to control the temperature of one or more components of the medical device 16 during operation of the system 10. In particular, the control unit 14 may regulate coolant delivery from the coolant source 53 to the distal portion of the medical device 16 to cryoadhesively engage the thermally-transmissive region 38 to a tissue selected or targeted for puncture. The control unit 14 may achieve the desired thermal regulation through the modification of one or more fluid delivery characteristics such as flow rate or fluid pressure by manipulation of the aforementioned pumps, valves, and controllers. Temperature regulation may be achieved (in addition to or alternatively to the fluid control) through the implementation of one or more active thermal elements coupled to the control unit 14 and/or medical device 16, such as one or more cooling components (such as, subcoolers, Peltier coolers, Joule-Thompson coolers, Stirling engine, or the like) and/or active heat sources (e.g., heating element, immersion heater, circulation heater, tubular heating element, cartridge heater, or other devices for warming fluids or gases). For example, as shown in FIG. 1B, the device 12 may include a thermo-electric cooler 25, such as a Peltier device, at a location proximal to the distal end 20 of the device 12. The thermo-electric cooler 25 may be located at a point within the system 10 between the coolant source and the distal end 20 of the device 12, upstream of the point at which coolant enters the distal end 20 of the device 12, such that the thermo-electric cooler 25 cools fluid traveling to the distal end 20 of the device 12. The thermo-electric cooler 25 may alternatively be in direct thermal communication with the thermally-transmissive region 38 to affect a temperature thereof. Accordingly, the thermo-electric cooler may operate to thermally regulate a fluid being delivered to the thermally-transmissive region 38, and/or may directly thermally affect or regulate a temperature of the thermally-transmissive region without any fluid flow. If the thermo-electric cooler 25 is included in the device 12, one or more connecting wires 27 may be disposed within the device 12 to place the thermo-electric cooler 25 in communication with the control unit 14.

The control unit 14 may be operated to maintain a temperature of the thermally-transmissive region 38 low enough to achieve effective cryoadhesion to a tissue region, while preventing unwanted permanent tissue injury associated with ablative or necrotic freezing. For example, the target temperature range may be between approximately 0° C. and approximately negative 30° C. (−30° C.).

Figure 3:
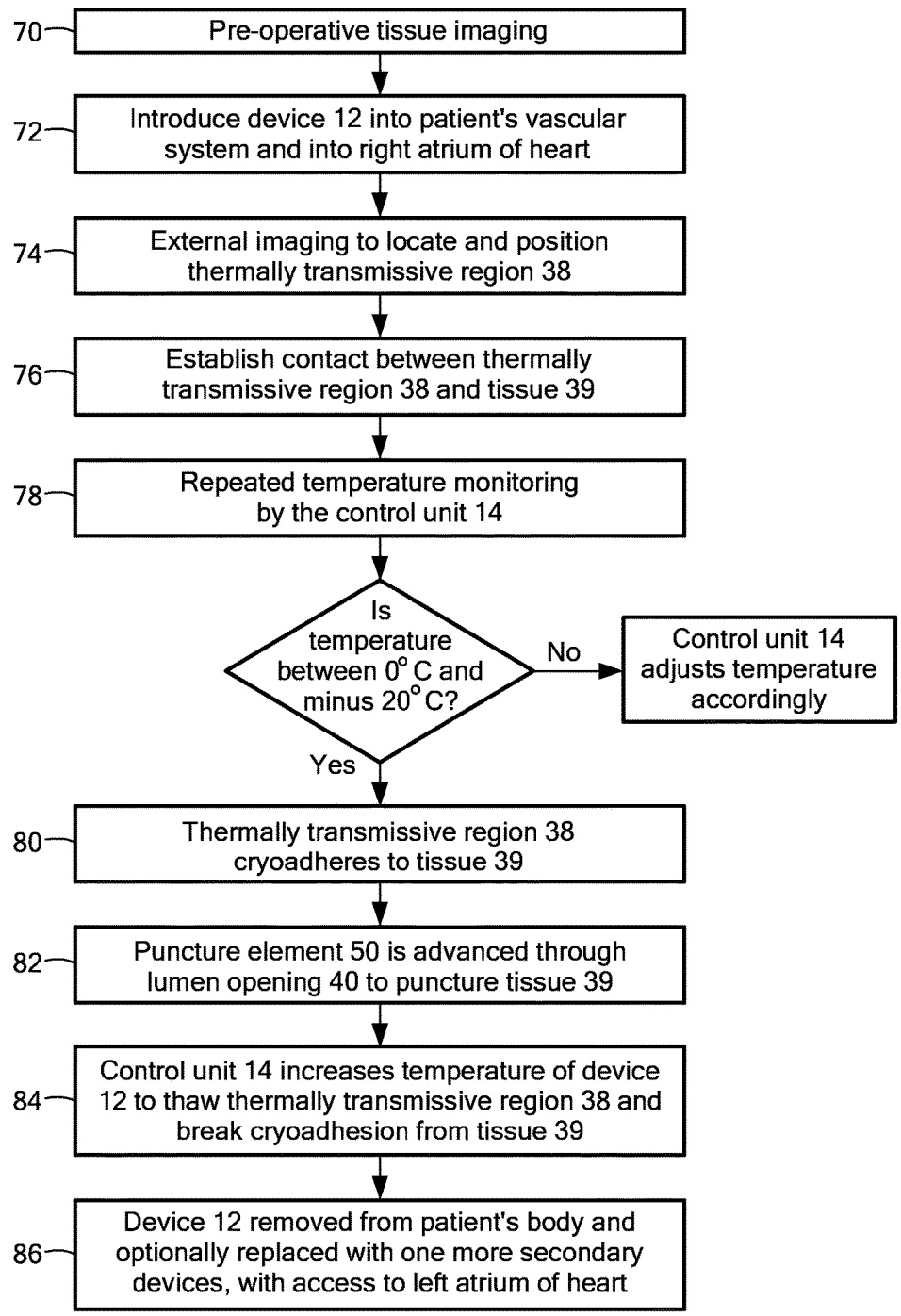
FIG. 3 is an example of a method for anchoring and puncturing tissue in accordance with the present disclosure.

Referring now to FIG. 3, an exemplary method of use of the system 10 is shown and includes cryoadehsively anchoring and puncturing tissue 39, while optionally monitoring and maintaining the temperature of a portion of the device 12 within a target temperature range. In particular, the tissue 39 may be imaged to identify any pre-existing anatomical abnormalities or complications, and to determine the optimal location for performing the puncture (Step 70). Such imaging may be performed using X-ray computed tomography (CT), magnetic resonance (MRI), angiography, or other non-invasive imaging methods. Access to the patient's vasculature may then be gained, through the femoral artery for example (Step 72). The device 12 may subsequently be advanced along the vasculature and towards the tissue targeted for puncture, which may include the right atrium of the heart, for example. The routing of the medical device may be facilitated in part by the guide wire 48. To prevent inadvertent laceration of tissue 39 (such as the superior vena cava (SVC), aortic valve and root) during this and subsequent steps, the puncturing element 50 may remain in the neutral position in which the tip of the puncturing element 50 is located within the device 12, away from the lumen opening 40 toward the proximal end 18 of the device 12.

Once in the general proximity of the targeted tissue site, an external imaging technique may be used to determine the location of the device 12 in relation to the tissue 39 to be punctured, which may include the septum (Step 74). The device 12 may be manipulated and repositioned as needed until the desired proximity to the targeted tissue is achieved. The one or more temperature sensors 42 and/or pressure sensors 46 on or in the device 12 may provide information to guide positioning. The thermally transmissive region 38 of the device 12 may be put in contact with tissue 39 (Step 76). The optimal location for contact may be determined using the imaging and sensory techniques described above.

Next, coolant may be delivered from the coolant source 53 to the medical device 12 to cool the thermally-transmissive region 38 within the target temperature range (approximately 0° C. to approximately −30° C.) in order to cryoadhere the device 12 to the tissue 39. The one or more temperature sensors 42 may measure and communicate to the control unit 14 the temperature of the thermally-transmissive region 38 and/or interface between the tissue 39 and thermally transmissive region 38 until the temperature is within the designated range (Steps 78, 80). The coolant delivery and/or temperature of the thermally-transmissive segment 38 may be continually monitored and regulated to maintain the temperature within the target temperature range to ensure sufficient cryoadhesion while preventing unwanted ablation or other permanent freezing injury. If the one or more temperature sensors 42 measure a temperature that is above or below the target temperature range, the control unit 14 may automatically adjust the flow and/or temperature of the coolant accordingly. Additionally or alternatively, the user interface 56, which may be in communication with the control unit 14, may be used to adjust temperature and/or fluid flow characteristics. The user interface 56 may be used to manually adjust the temperature of the device 12 within the target temperature range by manipulation of the control unit 14. Pressure between the medical device 16 and the tissue 39 may also be continually monitored to assess contact and engagement therebetween, with disruptions in measured pressure or a measured pressure falling outside of an expected value resulting in the automated termination of coolant delivery.

Following cryoadhesion of the distal portion 20 of the medical device 12 to the tissue 39, the puncturing element 50 may be advanced through the lumen opening 40 of the device 12 to puncture the tissue 39 (Step 82). The cryoadhesion between the thermally transmissive region 38 and the tissue 39 prevents the tissue 39 from significantly tenting or otherwise moving with respect to the medical device 12. This, in turn, may prevent the unintentional laceration of the tissue 39 or other complications arising from insufficient coupling between a puncturing device and the tissue, especially when dealing with the tortuous environment within the heart, for example. After the puncture, additional procedures may be performed to enhance patient safety or to ensure complete puncture. For example, blood may be aspirated through the device 12 to remove any air from the needle. Additionally, contrast may be injected from the device 12 into the left atrium to visualize the puncture.

The device may subsequently be warmed or thawed to allow the thermally transmissive region 38 to safely detach from the tissue 39 (i.e. break cryoadhesion) without damaging the tissue. The thawing may be performed actively by one or more heating components on the medical device 12 and/or may be done through heating from surrounding blood flow for a designated period of time.

After successfully puncturing the tissue, device 12 may be removed from the patient's body and replaced with one or more post-puncture or secondary devices, such as dilators, sheaths, catheters, valves, prostheses, or other devices for treatment, imaging, mapping, and/or diagnosis (Step 86). When the device 12 is removed, the guide wire 48 may be left in place to facilitate the placement of one or more secondary devices. For example, a dilator (not shown) may be positioned in the puncture using the guide wire 48. Then, a sheath and secondary device may also be advanced along the guide wire 48 across the septum, and into the left atrium. Alternatively, the device 12 may be left in place for the duration of the procedure, with the thermally-transmissive region 38 being maintained in the target temperature range (i.e. with the thermally-transmissive region 38 still cryoadhered to the septal region 39). This may help stabilize the septal region and prevent its rupture during the insertion and manipulation of the one or more secondary devices 88.

Figure 4:
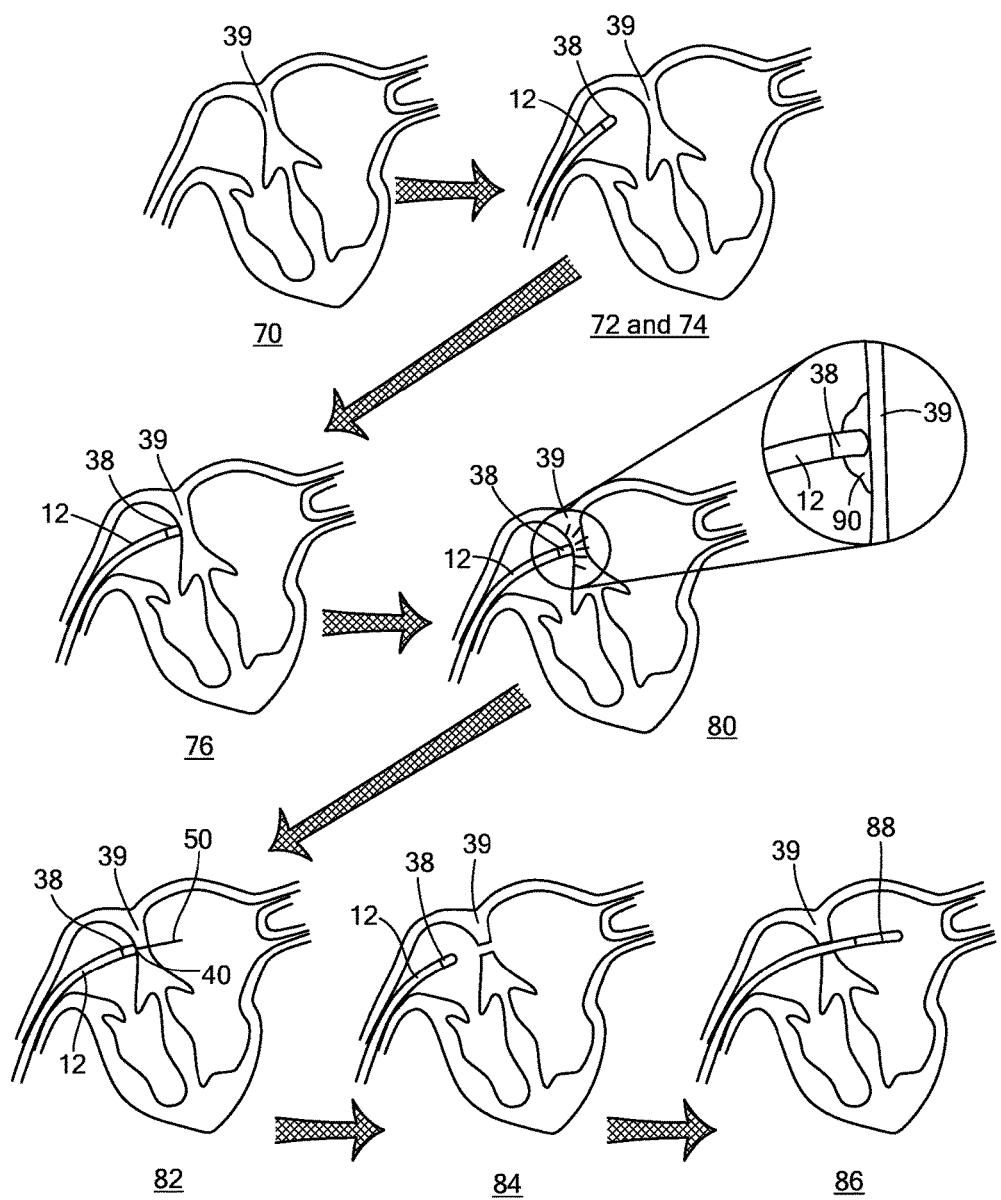
FIG. 4 is a graphical depiction of the method of FIG. 3.

An exemplary method of use of the system 10 is described in the flow chart of FIG. 3, with FIG. 4 illustrating an example of a method of use with respect to a cardiac region. The method includes cryoadehsively anchoring and puncturing tissue 39. In particular, the septal region of the heart 39 may be imaged (Step 70). Access to the patient's vasculature may then be gained, for example, through the femoral artery, and the device may subsequently be advanced along the vasculature into the right atrium of the heart (Step 72). Once in the general proximity of the targeted tissue site, an external imaging technique may be used to determine the location of the device 12 in relation to the septal region 39 (Step 74). The device 12 may be manipulated and repositioned as needed until the desired proximity to the septal region 39 is achieved. The thermally transmissive region 38 of the device 12 may be put in contact with septal region 39 (Step 76).

Next, coolant may be delivered from the coolant source 53 to the medical device 12 to cool the thermally-transmissive region 38 within the target temperature range (approximately 0° C. to approximately −30° C.) in order to cryoadhere the device 12 to the septal region 39 (Step 80). Ice (from freezing blood) 90 may form between the thermally-transmissive region 38 and the septal region 39 during cryoadhesion. The temperature of the thermally-transmissive region 38 may be continually monitored, as described in FIG. 3.

Following cryoadhesion of the distal portion 20 of the medical device 12 to the septal region 39, the puncturing element 50 may be advanced through the lumen opening 40 of the device 12 to puncture the septal region 39 (Step 82). The cryoadhesion between the thermally transmissive region 38 and the septal region 39 prevents the septal region 39 from significantly tenting or otherwise moving with respect to the medical device 12. This, in turn, may prevent the unintentional laceration of the septal region 39 (or other areas of the heart) or other complications arising from insufficient coupling between a puncturing device and the septal region.

The device may subsequently be warmed or thawed to allow the thermally transmissive region 38 to safely detach from the septal region 39 (i.e. break cryoadhesion) without damaging the tissue. The thawing may be performed actively by one or more heating components on the medical device 12 and/or may be done through heating from surrounding blood flow for a designated period of time.

After successfully puncturing the septal region 39, the device 12 may be removed from the patient's body and replaced with one or more post-puncture or secondary devices 88 (Step 86). When the device 12 is removed, the guide wire 48 may be left in place to facilitate the placement of one or more secondary devices 88. Alternatively, the device 12 may be left in place for the duration of the procedure, with the thermally-transmissive region 38 being maintained in the target temperature range (i.e. with the thermally-transmissive region 38 still cryoadhered to the septal region 39). This may help stabilize the septal region and prevent its rupture during the insertion and manipulation of the one or more secondary devices 88.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A tissue puncturing device, comprising:
an elongate body defining a longitudinal axis, a proximal portion, a distal portion, a fluid flow path, and a lumen being symmetrically disposed within the elongate body and being coaxial with the longitudinal axis;
a cryoadhesive segment coupled to the distal portion of the elongate body and in thermal communication with the fluid flow path, the cryoadhesive segment defining a distal face that is coaxial with the lumen; and
a puncturing element movably disposed within the lumen.

2. The tissue puncturing device of claim 1, further comprising a cryogenic coolant source in fluid communication with the fluid flow path.

3. The tissue puncturing device of claim 2, further comprising a sensor coupled to the distal portion of the elongate body.

4. The tissue puncturing device of claim 3, further comprising a control unit in communication with the sensor, the control unit programmed to regulate fluid flow to the fluid flow path based at least in part on a signal from the sensor.

5. The tissue puncturing device of claim 4, wherein the sensor is a temperature sensor.

6. The tissue puncturing device of claim 4, wherein the sensor is a pressure sensor.

7. The tissue puncturing device of claim 4, wherein the sensor is a flow rate sensor.

8. The tissue puncturing device of claim 4, wherein the control unit is programmed to maintain a temperature of the cryoadhesive segment within a predefined temperature range.

9. The tissue puncturing device of claim 4, wherein the predefined temperature range is between approximately 0° C. and approximately −30° C.

10. The tissue puncturing device of claim 4, wherein the device further includes a Peltier cooler.

11. The tissue puncturing device of claim 1, wherein the puncturing element is a needle.

12. The tissue puncturing device of claim 1, wherein the puncturing element is a guide wire.

13. The tissue puncturing device of claim 1, wherein the lumen is thermally insulated.

14. The tissue puncturing device of claim 1, wherein the cryoadhesive segment defines a distal face including a lumen opening, the tissue puncturing device further comprising one or more temperature sensors and one or more pressure sensors disposed on the distal face of the cryoadhesive segment and being radially spaced about the lumen opening.

15. The tissue puncturing device of claim 1, further comprising one or more heating elements in thermal communication with the cryoadhesive segment.

* * * * *